United States Patent
Horibe

(10) Patent No.: US 12,348,848 B2
(45) Date of Patent: Jul. 1, 2025

(54) IMAGE PICKUP UNIT AND INSERTION INSTRUMENT

(71) Applicant: OLYMPUS CORPORATION, Tokyo (JP)

(72) Inventor: Takuro Horibe, Funabashi (JP)

(73) Assignee: OLYMPUS CORPORATION, Tokyo (JP)

(*) Notice: Subject to any disclaimer, the term of this patent is extended or adjusted under 35 U.S.C. 154(b) by 283 days.

(21) Appl. No.: 18/078,435

(22) Filed: Dec. 9, 2022

(65) Prior Publication Data

US 2023/0111466 A1 Apr. 13, 2023

Related U.S. Application Data

(63) Continuation of application No. PCT/JP2020/030244, filed on Aug. 6, 2020.

(51) Int. Cl.
*H04N 23/50* (2023.01)
*A61B 1/05* (2006.01)
*H04N 23/51* (2023.01)
*H04N 23/55* (2023.01)

(52) U.S. Cl.
CPC ............. *H04N 23/555* (2023.01); *A61B 1/05* (2013.01); *H04N 23/51* (2023.01); *H04N 23/55* (2023.01)

(58) Field of Classification Search
CPC .................................................. H04N 23/555
See application file for complete search history.

(56) References Cited

U.S. PATENT DOCUMENTS

| | | | | |
|---|---|---|---|---|
| 7,453,509 B2* | 11/2008 | Losehand | ............... | H01L 24/97 257/E31.127 |
| 2003/0203532 A1 | 10/2003 | Misawa | | |
| 2005/0024529 A1* | 2/2005 | Kurosawa | ............. | H04N 23/54 257/E27.151 |
| 2006/0028573 A1* | 2/2006 | Seo | ........................ | H04N 23/55 348/340 |
| 2009/0010140 A1* | 1/2009 | Ishii | ........................ | A61B 1/05 |
| 2009/0067830 A1 | 3/2009 | Tamaki et al. | | |
| 2009/0152658 A1* | 6/2009 | Bolken | ............. | H01L 27/14625 257/E31.127 |
| 2009/0253955 A1 | 10/2009 | Akiba | | |
| 2010/0231766 A1 | 9/2010 | Moriya et al. | | |

(Continued)

FOREIGN PATENT DOCUMENTS

| | | | |
|---|---|---|---|
| EP | 1 920 708 A1 | 5/2008 |
| EP | 3 130 275 A1 | 2/2017 |

(Continued)

OTHER PUBLICATIONS

International Search Report dated Oct. 6, 2020 received in PCT/JP2020/030244.

*Primary Examiner* — Cynthia Segura
(74) *Attorney, Agent, or Firm* — Scully, Scott, Murphy & Presser, P.C.

(57) ABSTRACT

An image pickup unit includes a distal end member including a recess portion, an image pickup device unit, and an objective lens unit. The recess portion is formed such that a spatial cross-sectional area of the recess portion increases continuously or stepwise from a bottom surface toward an opening. The objective lens unit is fixed to the recess portion by a sealing material injected in a gap.

20 Claims, 15 Drawing Sheets

(56) References Cited

U.S. PATENT DOCUMENTS

| | | | | |
|---|---|---|---|---|
| 2010/0259657 | A1* | 10/2010 | Lee | H01L 27/14618 |
| | | | | 348/294 |
| 2010/0295178 | A1* | 11/2010 | Ishihara | H05K 1/187 |
| | | | | 257/737 |
| 2017/0064164 | A1* | 3/2017 | Nishihara | A61B 1/00045 |
| 2017/0082077 | A1* | 3/2017 | Kato | F02M 61/1833 |
| 2017/0307872 | A1* | 10/2017 | Hatase | A61B 1/0684 |
| 2020/0178779 | A1* | 6/2020 | Komoro | A61B 1/05 |

FOREIGN PATENT DOCUMENTS

| | | |
|---|---|---|
| JP | S60-203230 A | 10/1985 |
| JP | 2004-007499 A | 1/2004 |
| JP | 2006-154319 A | 6/2006 |
| JP | 2007-068563 A | 3/2007 |
| JP | 2010-213034 A | 9/2010 |
| JP | 5042481 B2 | 10/2012 |
| JP | 2013-078440 A | 5/2013 |
| JP | 2013-098182 A | 5/2013 |
| JP | 2016-086068 A | 5/2016 |
| JP | 2017-074257 A | 4/2017 |
| WO | 2007/123064 A1 | 1/2007 |
| WO | 2015/174406 A1 | 11/2015 |

* cited by examiner

IMAGE PICKUP UNIT AND INSERTION INSTRUMENT

CROSS REFERENCE TO RELATED APPLICATION

This application is a continuation application of PCT/JP2020/030244 filed on Aug. 6, 2020, the entire contents of which are incorporated herein by this reference.

BACKGROUND OF THE INVENTION

1. Field of the Invention

The present invention relates to an image pickup unit including an objective lens unit and an image pickup device unit that are fixed in a recess portion of a housing member of the image pickup unit, and also relates to an insertion instrument.

2. Description of the Related Art

In recent years, electronic endoscope apparatuses have been widely spread. Such electronic endoscope apparatuses include an image pickup unit provided in a distal end portion of an insertion portion of an insertion instrument, for example, an endoscope, and are configured to be capable of observing an image of an object in a subject on a monitor by inserting the insertion portion in which the image pickup unit is provided into the subject.

Japanese Patent No. 5042481 discloses a configuration in which an image pickup unit including a focus-adjusted objective lens unit and an image pickup device unit is inserted from a proximal end side of an external shape adjusting member into a through hole of the external shape adjusting member and fixed thereto, and the external shape adjusting member is fixed to a through hole of a distal end member provided at a distal end portion of an insertion portion of an endoscope, to thereby fix the image pickup unit in the distal end portion.

In addition, an image pickup device is fixed to a device frame, with a cover glass interposed therebetween, and thereafter fixed to the external shape adjusting member, to be further fixed to the distal end member.

SUMMARY OF THE INVENTION

An image pickup unit according to one aspect of the present invention includes: a housing member including a recess portion that includes an opening at one end of the recess portion and a bottom surface at another end of the recess portion, the recess portion being formed along a longitudinal axis direction connecting the one end and the other end; an image pickup device unit configured to pick up an image of an object, the image pickup device unit being fixed to the bottom surface of the recess portion; and an objective lens unit including a lens configured to form an image of light from the object and a holding frame configured to hold the lens, the objective lens unit being housed in the recess portion and fixed to the recess portion at a set position where a focus adjustment including a tilt angle adjustment of the lens with respect to the image pickup device unit is performed. The recess portion is formed along the longitudinal axis direction such that a spatial cross-sectional area of the recess portion increases continuously or stepwise from the bottom surface toward the opening, and the objective lens unit is fixed to the recess portion by a sealing material injected in a gap formed in a radial direction of the objective lens unit, the radial direction being a direction orthogonal to the longitudinal axis direction.

An insertion instrument according to one aspect of the present invention includes an image pickup unit. The image pickup unit includes: a housing member including a recess portion that includes an opening at one end of the recess portion and a bottom surface at another end of the recess portion, the recess portion being formed along a longitudinal axis direction connecting the one end and the other end; an image pickup device unit configured to pick up an image of an object, the image pickup device unit being fixed to the bottom surface of the recess portion; and an objective lens unit including a lens configured to form an image of light from the object and a holding frame configured to hold the lens, the objective lens unit being housed in the recess portion and fixed to the recess portion at a set position where a focus adjustment including a tilt angle adjustment of the lens with respect to the image pickup device unit is performed. The recess portion is formed along the longitudinal axis direction such that a spatial cross-sectional area of the recess portion increases continuously or stepwise from the bottom surface toward the opening, and the objective lens unit is fixed to the recess portion by a sealing material injected in a gap formed in a radial direction of the objective lens unit, the radial direction being a direction orthogonal to the longitudinal axis direction.

DETAILED DESCRIPTION OF THE PREFERRED EMBODIMENT(S)

Hereinafter, embodiments of the present invention will be described with reference to drawings. Note that, in the embodiments to be described below, description will be made on an insertion instrument by taking an endoscope as an example.

First Embodiment

Figure 1:
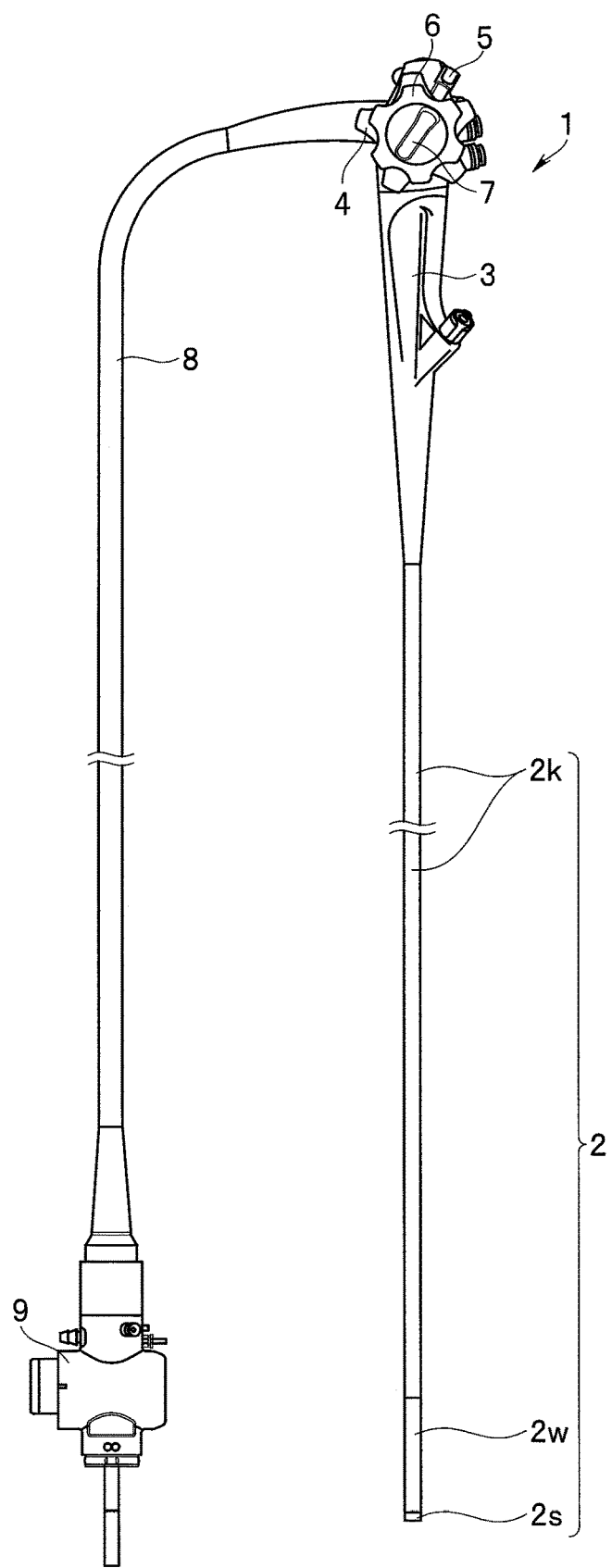
FIG. 1 is a view showing an appearance of an endoscope including, in a distal end portion of an insertion portion thereof, an image pickup unit according to a first embodiment.

FIG. 1 is a view showing an appearance of an endoscope including, in a distal end portion of an insertion portion thereof, an image pickup unit according to the present embodiment.

As shown in FIG. 1, an endoscope 1 has a main part configured by including: an insertion portion 2 configured to be inserted into a subject; an operation portion 3 provided continuously with a proximal end side of the insertion portion 2; a universal cord 8 extended from the operation portion 3; and a connector 9 provided at an extension end of the universal cord 8.

Note that the endoscope 1 is electrically connected to external apparatuses such as a control apparatus and an illumination apparatus, through the connector 9.

The operation portion 3 is provided with a bending knob 4 and a bending knob 6. The bending knob 4 is configured to bend a bending portion 2w, to be described later, of the insertion portion 2 in up and down directions. The bending knob 6 is configured to bend the bending portion 2w in left and right directions. Furthermore, the operation portion 3 includes a fixing lever 5 and a fixing knob 7. The fixing lever 5 is configured to fix a rotation position of the bending knob 4. The fixing knob 7 is configured to fix a rotation position of the bending knob 6.

The insertion portion 2 is configured of a distal end portion 2s, the bending portion 2w, and a flexible tube portion 2k, and is formed in an elongated shape along a longitudinal axis direction of the insertion portion 2.

The distal end portion 2s includes, inside thereof, an image pickup unit 10 (see FIG. 2), to be described later, configured to observe an inside of a subject, an illumination unit, not shown, configured to illuminate the inside of the subject, and the like.

The bending portion 2w is configured to be bent in four directions, for example, up, down, left, and right directions, by rotational operations of the bending knob 4 and the bending knob 6, to thereby vary the observation direction of the image pickup unit 10 provided in the distal end portion 2s and improve an insertion performance of the distal end portion 2s in the subject. Furthermore, the flexible tube portion 2k is provided continuously with a proximal end side of the bending portion 2w.

Next, description will be made on a configuration of the image pickup unit 10 provided in the distal end portion 2s, with reference to FIGS. 2 to 4.

Figure 2:
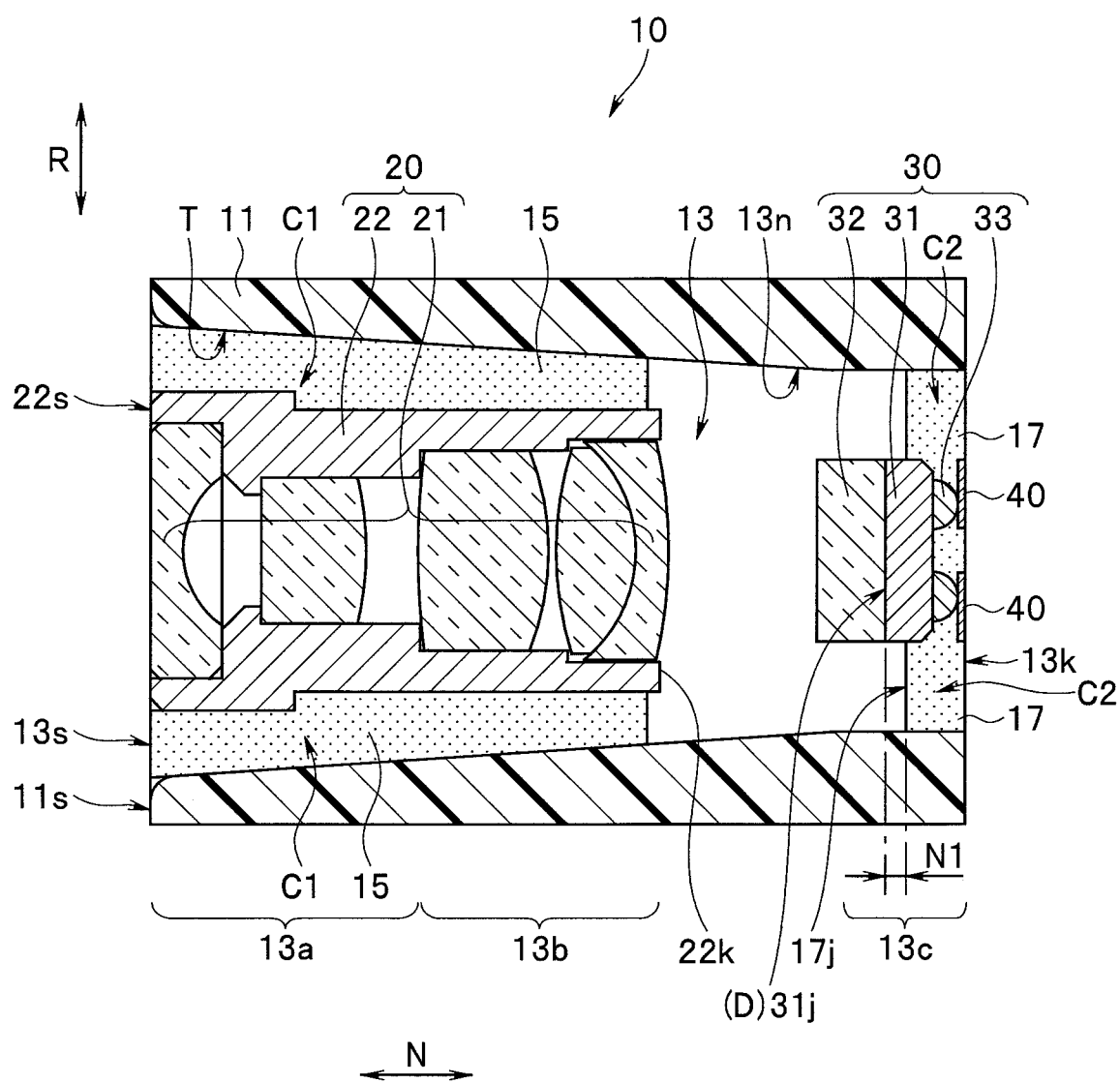
FIG. 2 is a cross-sectional view showing an outline of a configuration of the image pickup unit provided in the distal end portion of the insertion portion in the endoscope in FIG. 1.

FIG. 2 is a cross-sectional view showing an outline of the configuration of the image pickup unit provided in the distal end portion of the insertion portion in the endoscope in FIG. 1. FIG. 3 is a partial cross-sectional view showing a state where a cable is connected to a housing member in the image pickup unit in FIG. 2. FIG. 4 is a partial cross-sectional view showing a state where an objective lens unit is inserted into a recess portion of the housing member in the image pickup unit in FIG. 3 by using a grasping jig.

As shown in FIG. 2, the image pickup unit 10 has a main part configured by including a distal end member 11 as the housing member, an objective lens unit 20, and an image pickup device unit 30.

Note that the distal end member 11 is configured of a distal end rigid member constituting the distal end portion 2s, for example, and is made of resin, for example.

The distal end member 11 includes a recess portion 13. The recess portion 13 includes at one end thereof an opening 13s and at another end thereof a bottom surface 13k. The recess portion 13 is formed along a longitudinal axis direction N connecting the one end and the other end, and the bottom surface 13k constitutes a bottom portion 11b (see FIG. 3) of the distal end member 11. The objective lens unit 20 and the image pickup device unit 30 are fixed to an inside of the recess portion 13.

The recess portion 13 is formed in a shape in which the spatial cross-sectional area thereof increases continuously or stepwise from the bottom surface 13k toward the opening 13s along the longitudinal axis direction N.

Specifically, the recess portion 13 includes a large-diameter region 13a, a small-diameter region 13b, and a terminal fixing region 13c.

The large-diameter region 13a is formed, from the opening 13s toward the bottom surface 13k, up to a middle position of the objective lens unit 20 in the longitudinal axis direction N. The objective lens unit 20 is fixed at a set position, to be described later, in the recess portion 13.

In addition, the small-diameter region 13b is formed, from the above-described middle position toward the bottom surface 13k, up to an end portion 22k of a lens frame 22 to be described later. The end portion 22k is an end portion of the objective lens unit 20 and faces the bottom surface 13k.

Note that, in the present embodiment, the large-diameter region 13a and the small-diameter region 13b are continuous in the longitudinal axis direction N on an inner peripheral surface 13n of the recess portion 13, to form a tapered surface T, and have a spatial shape in which the spatial cross-sectional area increases continuously toward the opening 13s.

Furthermore, the terminal fixing region 13c is located on a side closer to the bottom surface 13k than the small-diameter region 13b in the longitudinal axis direction N and formed up to the bottom surface 13k. The terminal fixing region 13c forms an inner peripheral surface along the longitudinal axis direction N in the recess portion 13, and has a constant spatial cross-sectional area.

The image pickup device unit 30 is configured to pick up an image of an object through the objective lens unit 20. The image pickup device unit 30 is inserted from the opening 13s into the recess portion 13 to be fixed to the bottom surface 13k.

Specifically, the image pickup device unit 30 includes an image pickup device 31, a cover glass 32 as a sealing glass, and two connection terminals 33.

The image pickup device 31 is fixed in the recess portion 13 at an image forming position of a lens 21, to be described later, of the objective lens unit 20, and configured of a known CCD, CMOS, and the like.

The cover glass 32 is configured to protect a light-receiving surface 31j of the image pickup device 31 and fixed onto the light-receiving surface 31j with an adhesive, or the like.

The connection terminals 33 are provided on a surface of the image pickup device 31, the surface being opposite to the light-receiving surface 31j in the longitudinal axis direction N. In the terminal fixing region 13c, the connection terminals 33 are electrically connected respectively to mounting terminals 40 formed integrally with the bottom surface 13k. Thus, the image pickup device unit 30 is fixed to the bottom surface 13k.

Note that the distal end member 11 is an MID (molded interconnect device) as described above, in which the mounting terminals 40 are formed on the bottom surface 13k of the recess portion 13 by laser drawing and plating thereafter, and the like.

Figure 3:
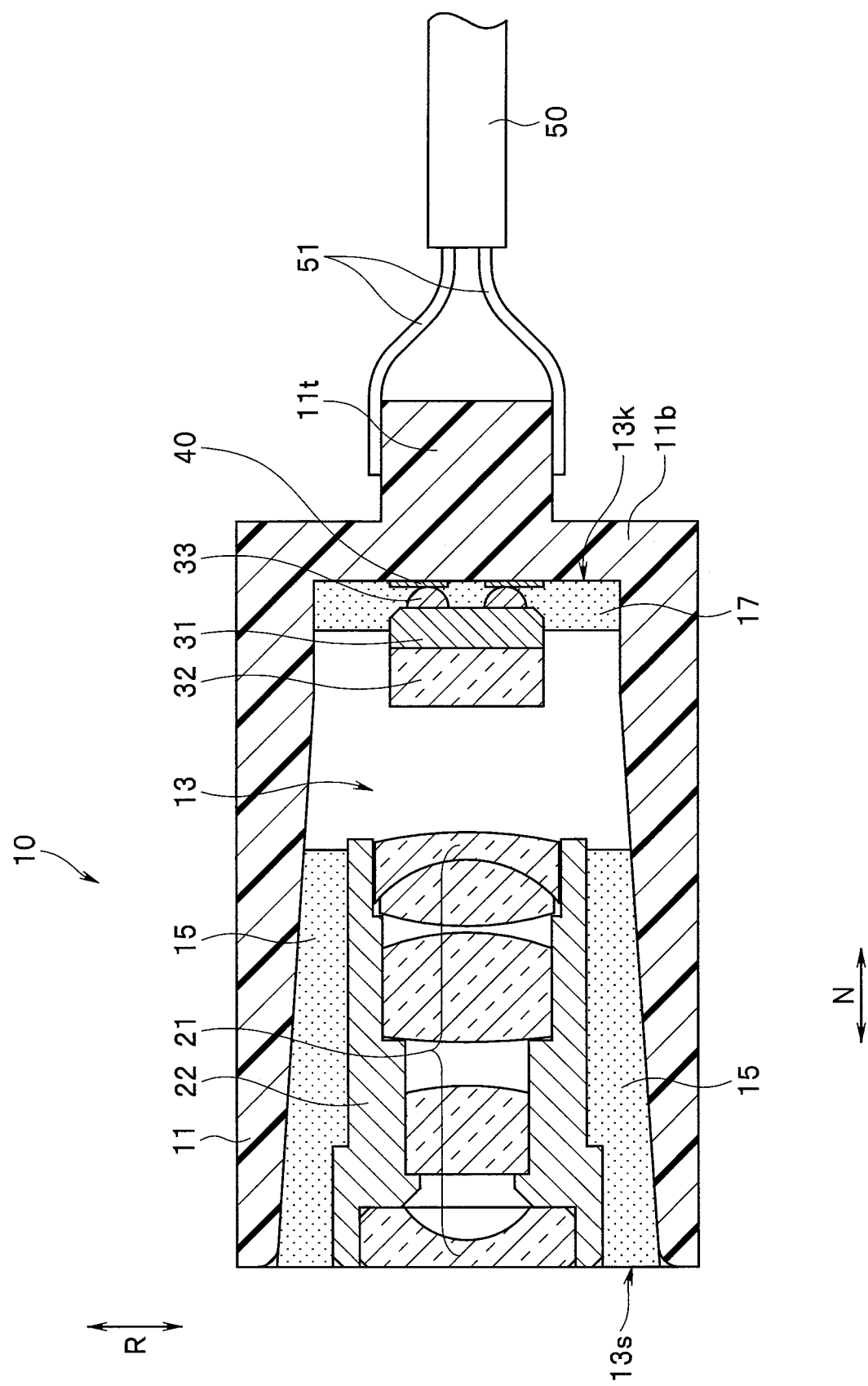
FIG. 3 is a partial cross-sectional view showing a state where a cable is connected to a housing member in the image pickup unit in FIG. 2.

In addition, as shown in FIG. 3, the distal end member 11 includes a protruding portion 11t protruding from the bottom portion 11b in the longitudinal axis direction N. At the protruding portion 11t, a signal line 51 of a cable 50 is electrically connected to a wiring 88 (see FIG. 11), to be described later, which is electrically connected to the mounting terminals 40. The cable 50 is configured to transmit and receive a signal to and from the image pickup device 31 through the signal line 51, the wiring 88, the mounting terminals 40, and connection terminals 33.

In addition, in the terminal fixing region 13c, another sealing material 17, which is different from a sealing material 15 to be described later, is injected into a gap C2, to be described later, formed in a radial direction R. The gap C2 is formed between the inner peripheral surface 13n of the recess portion 13 and a part where the image pickup device 31, the connection terminals 33, and mounting terminals 40 are provided.

The other sealing material 17 covers the peripheries of the connection terminals 33 to protect the connection terminals 33, in order to prevent the sealing material 15, to be described later, from adhering to the connection terminals 33. Note that also the part between the two connection terminals 33 may be filled with the other sealing material 17.

In addition, the other sealing material 17 is injected such that a filled surface 17j located on the opening 13s side in the longitudinal axis direction N is positioned on the side closer to the bottom surface 13k by a distance N1 in the longitudinal axis direction N than a bonding surface D of the image pickup device 31 and the cover glass 32.

With such a configuration, when the other sealing material 17 is injected into the gap C2 by an injection method to be described later, the other sealing material 17 is prevented from adhering to a boundary portion including the bonding surface D. As a result, only the peripheries of the connection terminals 33 are filled with the other sealing material 17.

Therefore, a stress accompanying a cure shrinkage of the other sealing material 17 is not directly applied to the bonding surface D, to thereby prevent separation of the cover glass 32 on the bonding surface D.

The objective lens unit 20 includes the lens 21, and the lens frame 22 as a holding frame.

The lens 21 is configured to form an image of light from the object, and is constituted of one or a plurality of lenses. In the case w % here the lens 21 is constituted of a plurality of lenses, the lens 21 may include a prism.

The lens frame 22 is configured to hold the lens 21. Note that the lens frame 22 is not limited to one frame, but may be constituted of two or more frames.

The objective lens unit 20 is fixed in the recess portion 13 at the set position where a focus adjustment is performed on the objective lens unit 20. The focus adjustment includes a tilt angle adjustment of the lens 21 with respect to the image pickup device 31.

Figure 4:
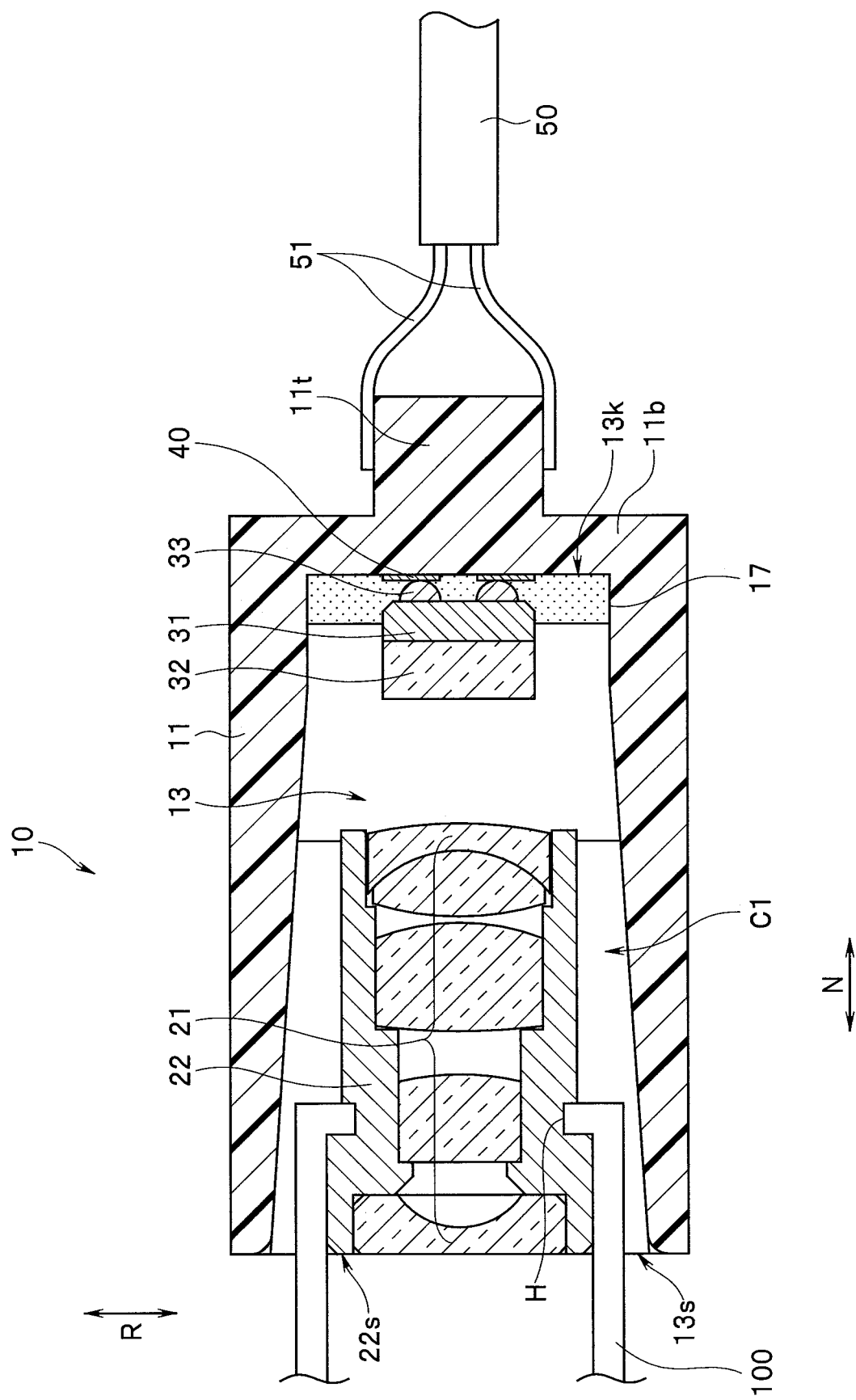
FIG. 4 is a partial cross-sectional view showing a state where an objective lens unit is inserted into a recess portion of the housing member in the image pickup unit in FIG. 3 by using a grasping jig.

Note that, as shown in FIG. 4, a grasping jig 100 is inserted from the opening 13s into the large-diameter region 13a of the recess portion 13, in the state of grasping the lens frame 22 of the objective lens unit 20, to thereby allow the objective lens unit 20 to be disposed in the recess portion 13.

Therefore, the large-diameter region 13a configures a space into which the grasping jig 100 is inserted, when the objective lens unit 20 is housed and fixed to the set position in the recess portion 13.

The space for allowing the grasping jig 100 to grasp the lens frame 22 is thus ensured in the recess portion 13, to thereby enable the positional adjustment and fixation of the lens frame 22 by using the grasping jig 100 in the recess portion 13.

In addition, the grasping jig 100 may include a grasping portion formed in accordance with a shape of a grasped portion (H) of the lens frame 22.

Note that the grasped portion H is not necessarily provided on the entire periphery of the lens frame 22, but has only to be provided at an appropriate position in accordance with the arrangement positions of a treatment instrument insertion conduit, not shown, formed in the distal end member 11, an illumination unit, a gas/liquid feeding conduit, and the like provided in the distal end member 11. In other words, the large-diameter region 13a may be provided only at a position not interfering with the above-described members when the grasped portion H is grasped by the grasping jig 100.

The objective lens unit 20 is fixed at the above-described set position in the recess portion 13 by the sealing material 15 injected in a gap C1 in the radial direction R of the objective lens unit 20, that is, between the outer surface of the objective lens unit 20 and the tapered surface T of the distal end member 11.

More specifically, the objective lens unit 20 is fixed to the recess portion 13 at the set position by the sealing material 15 injected in the gap C1 between the objective lens unit 20 and the large- and small-diameter regions 13a and 13b in the radial direction R.

Note that the description on the method of fixing the objective lens unit 20 to the recess portion 13 will be omitted.

Next, description will be made on a configuration for injecting the other sealing material 17 into the gap C2, with reference to FIG. 5 and FIG. 6.

Figure 5:
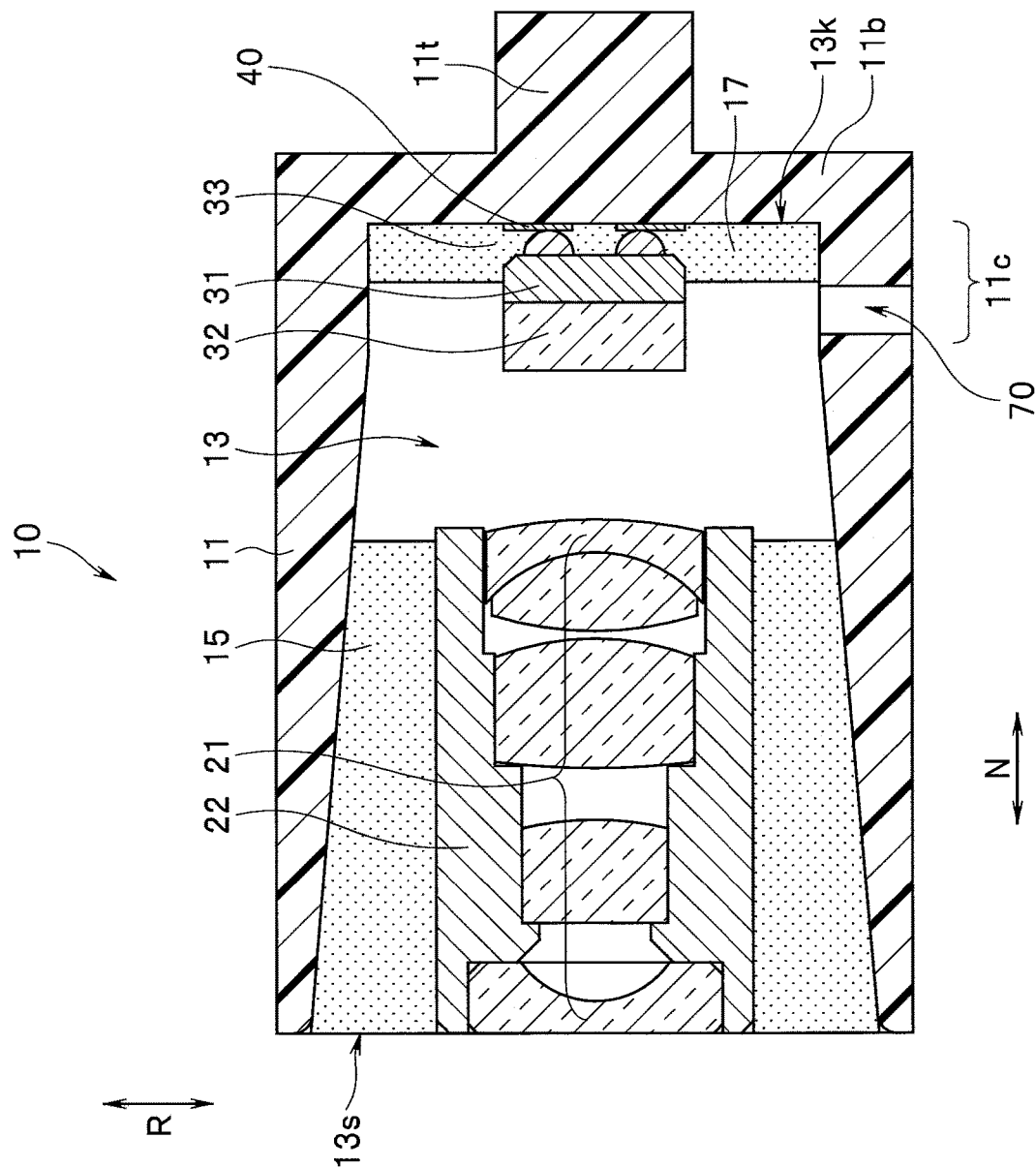
FIG. 5 is a cross-sectional view showing a configuration of the image pickup unit in which an injection hole is formed in a part where a terminal fixing region is formed in a distal end member in FIG. 3, with the cable and a signal line being omitted.

FIG. 5 is a cross-sectional view showing the configuration of the image pickup unit in which an injection hole is formed in the part where the terminal fixing region is formed in the distal end member in FIG. 3, with the cable and the signal line being omitted. FIG. 6 is a perspective view showing, in a cross section, a part of the distal end member including the recess portion, which is shown in FIG. 5.

Figure 6:
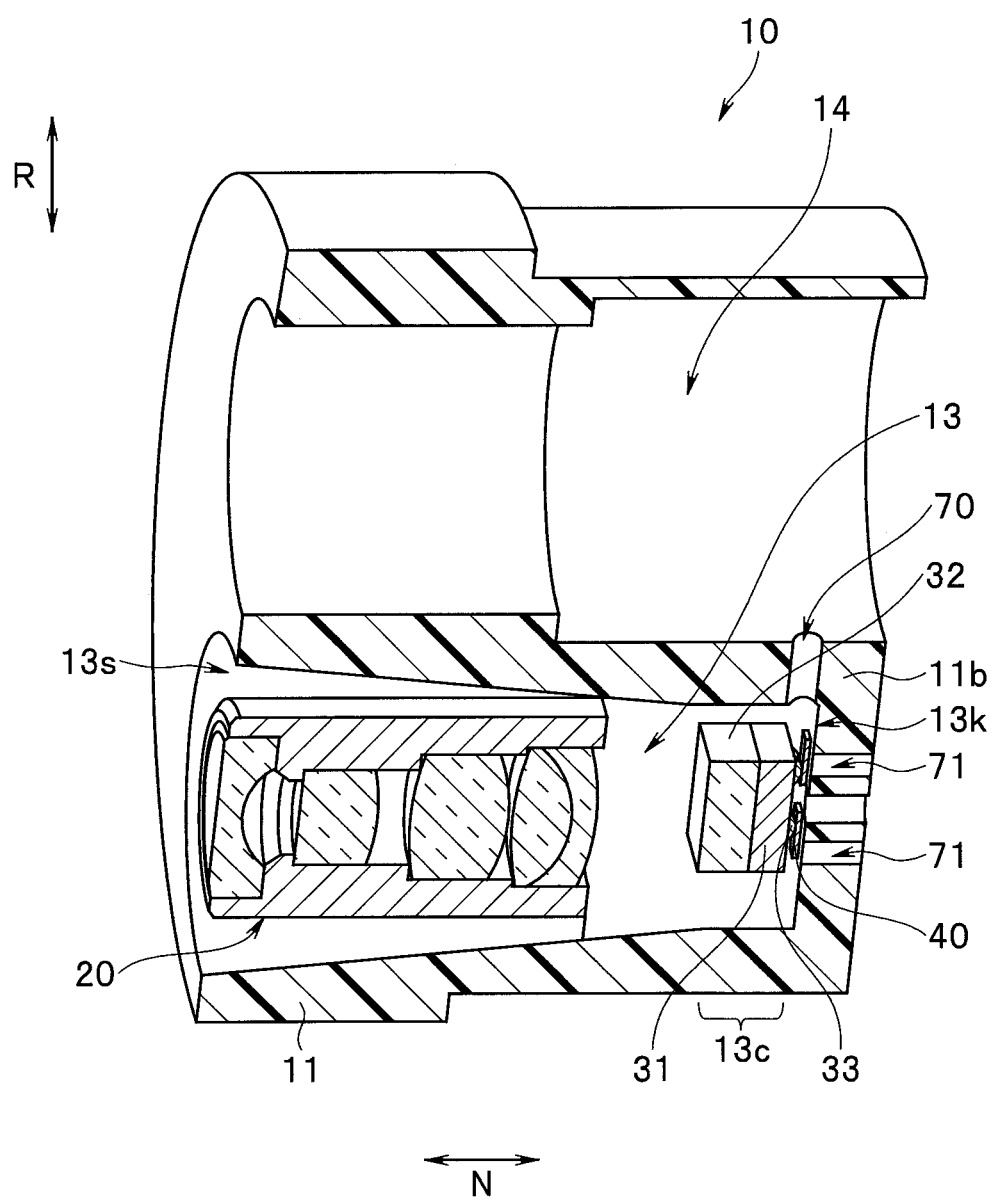
FIG. 6 is a perspective view showing, in a cross section, a part of the distal end member including the recess portion which is shown in FIG. 5.

As shown in FIGS. 5 and 6, the distal end member 11 includes, in the part where the terminal fixing region 13c is formed, an injection hole 70 through which the other sealing material 17 is injected into the gap C2 in the recess portion 13. The injection hole 70 is formed so as to penetrate the distal end member 11 in the radial direction R.

Note that, as shown in FIG. 6, the injection hole 70 may communicate with a through hole 14 which is formed in the distal end member 11 along the longitudinal axis direction N and which is different from the recess portion 13. In addition, the injection hole 70 may be constituted of two or more holes.

Furthermore, as shown in FIG. 6, injection holes 71, through each of which the other sealing material 17 is injected into the gap C2 in the recess portion 13, may be formed on the bottom portion 11b of the distal end member 11, so as to penetrate the bottom portion 11b in the longitudinal axis direction N.

Note that also the injection holes 71 are not limited to the two holes as shown in FIG. 6, but may be constituted of one, or three or more holes.

In addition, both or only one of the injection hole 70 and the injection hole 71 may be formed on the distal end member 11.

The image pickup unit 10 according to the present embodiment thus has a configuration in which the injection holes 70 and 71 are used for injecting the other sealing material 17 into the gap C2. Such a configuration enables the other sealing material 17 to be injected into the recess portion 13 not from the opening 13s side but from the bottom surface 13k side.

Such a configuration enables the other sealing material 17 to be surely injected into the gap C2 located at a deep position with respect to the opening 13s in the longitudinal axis direction N, to thereby be capable of surely sealing the peripheries of the connection terminals 33 by the other sealing material 17.

In addition, the other sealing material 17 can be injected from the radial direction R side and the bottom surface 13k side. Such a configuration prevents intrusion of air bubbles into the rear surface of the image pickup device 31 and a space between the connection terminals 33 during the injection of the other sealing material 17.

Such a configuration can thus prevent a connection failure of the connection terminals 33 to the mounting terminals 40 due to a volume expansion of air bubbles (void) in a high temperature, which improves the reliability of the connection strength.

Here, with reference to FIG. 7, description will be made on a modification of the forming position of the injection hole 70 in the distal end member 11.

Figure 7:
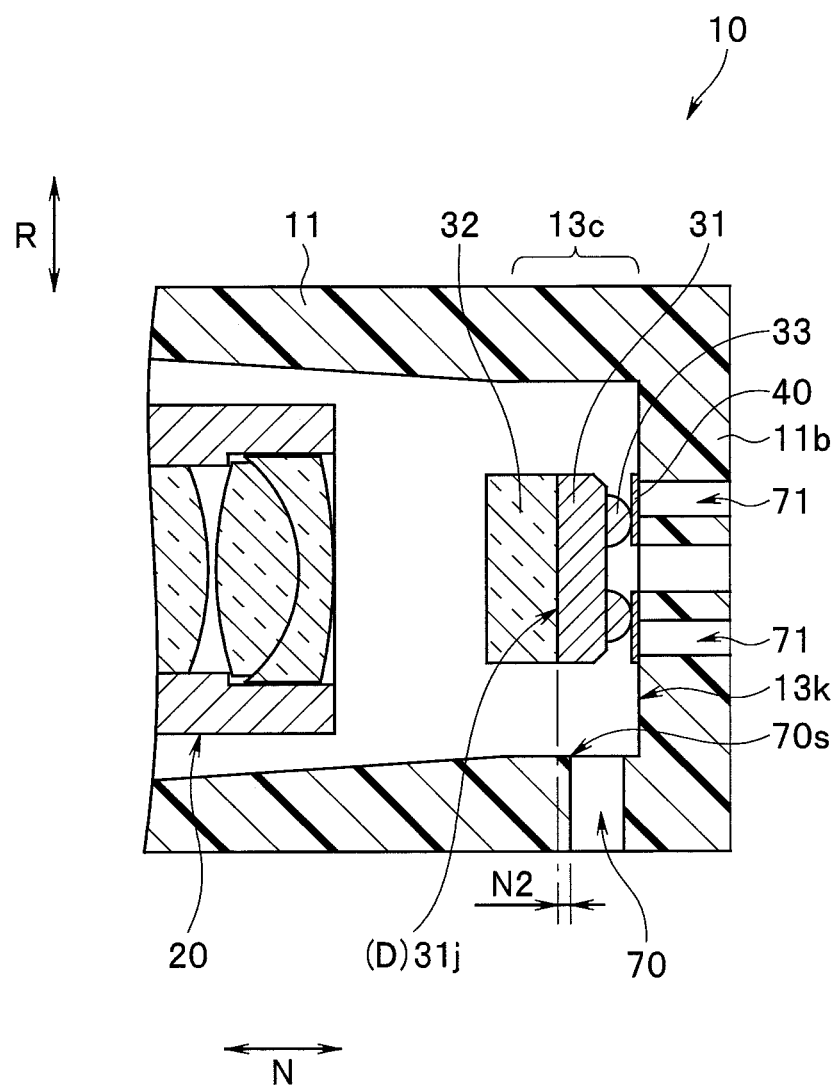
FIG. 7 is a partial cross-sectional view showing a modification of a forming position of the injection hole formed in the terminal fixing region in the distal end member in FIG. 5.

FIG. 7 is a partial cross-sectional view showing the modification of the forming position of the injection hole formed in the terminal fixing region in the distal end member in FIG. 5.

As shown in FIG. 7, the injection hole 70 may be formed in the part where the terminal fixing region 13c is formed in the distal end member 11 such that a position on the opening side of the recess portion 13, that is, a position 70s on the opening 13s side in the longitudinal axis direction N may be positioned on the side closer to the bottom surface 13k, by a distance N2, than the bonding surface D.

With such a configuration, the other sealing material 17 injected into the recess portion 13 through the injection hole 70 does not adhere to the boundary portion including the bonding surface D and to the cover glass 32. Thus, deterioration in image quality and the above-described separation of the bonding surface D, which are caused by the other sealing material 17 adhering to the cover glass 32, are prevented.

Furthermore, the other sealing material 17 can be injected from the side close to the bottom surface 13k, air bubbles hardly intrude into the rear surface of the image pickup device 31 and between the connection terminals 33, compared with the configurations shown in FIGS. 5 and 6. As a result, the reliability of the connection strength of the connection terminals 33 to the mounting terminals 40 is further improved.

Figure 8:
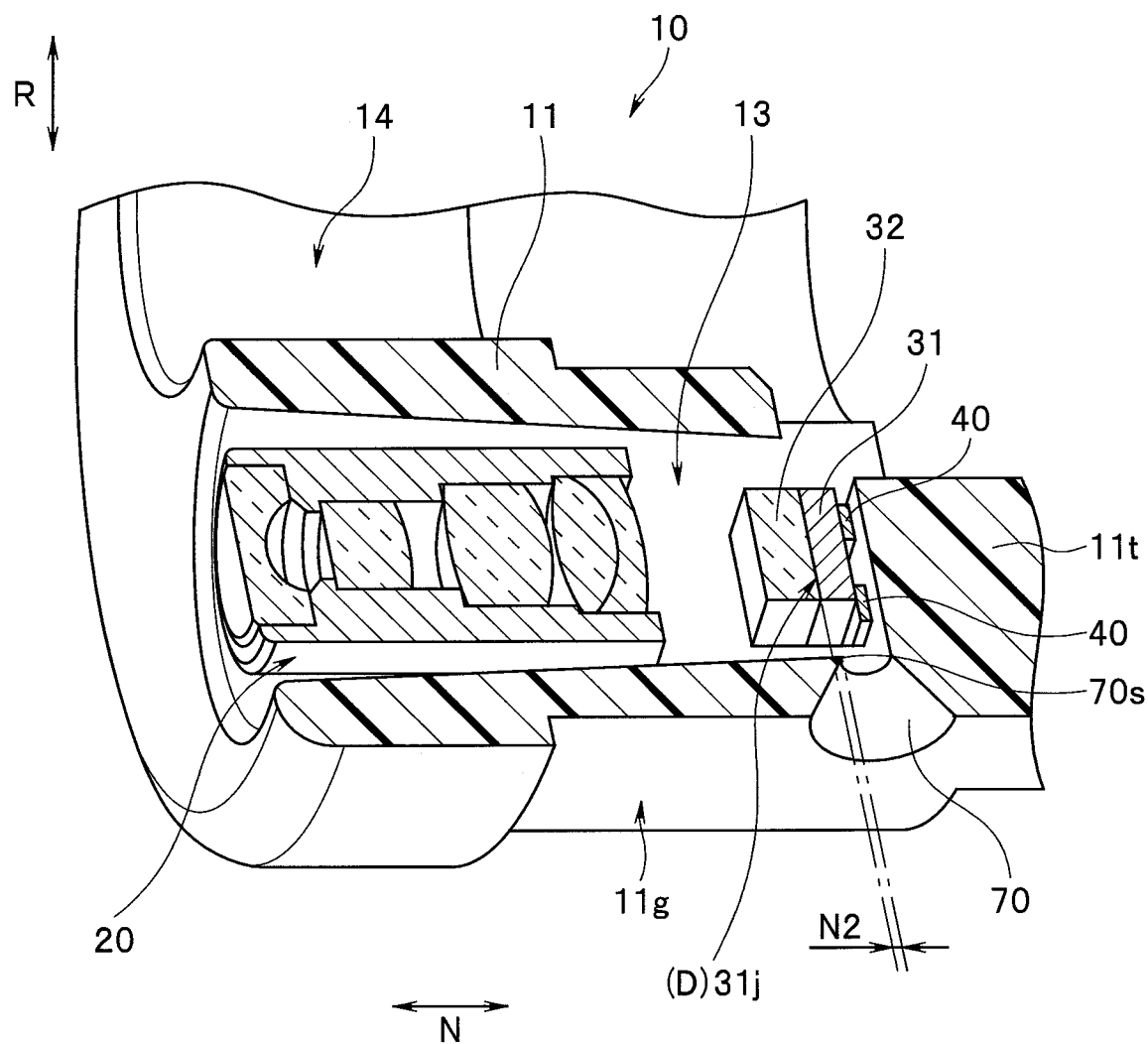
FIG. 8 is a perspective view showing a modification of a shape of the injection hole in FIG. 7, with a part of the distal end member shown in a cross section.

Next, with reference to FIG. 8, description will be made on a modification of the shape of the injection hole 70 in FIG. 7. FIG. 8 is a perspective view showing a modification of the shape of the injection hole in FIG. 7, with a part of the distal end member shown in a cross section.

As shown in FIG. 8, the injection hole 70 may be formed in a shape in which a cross section of the opening increases continuously from the recess portion 13 toward an outer peripheral surface 11g of the distal end member 11.

Note that, in the present configuration, similarly as in the above-described configuration shown in FIG. 7, the injection hole 70 is formed such that the position 70s, which is on the recess portion 13 side and which is on the opening 13s side in the longitudinal axis direction N, is located on the side closer to the bottom surface 13k, by the distance N2, than the bonding surface D.

If the sealing height (width) in the gap C2 in the longitudinal axis direction N is 0.3 mm, for example, it is preferable that the inner diameter of the opening, which is on the recess portion 13 side, of the injection hole 70 is equal to or smaller than 0.3 mm.

In addition, a diameter of an injecting portion of an injection tool such as a syringe, dispenser, or the like, for injecting the other sealing material 17 is generally 0.4 mm or larger.

Therefore, when the other sealing material 17 is injected through the injection hole 70, there is no choice but to use an injection tool having an injecting portion whose outer diameter is larger than the inner diameter of the opening, which is on the recess portion 13 side, of the injection hole 70.

If the injection hole 70 is formed in the shape as shown in FIG. 8, the other sealing material 17 can easily be injected by using an injection tool, from a large-diameter opening, which is located on the outer peripheral surface 11g, of the injection hole 70. Such a configuration improves the injecting performance, and in addition, enables the other sealing material 17 to be surely injected also into the gap C2 having a restriction in the height (thickness) in the longitudinal axis direction N as described above, while preventing the other sealing material 17 from adhering to the bonding surface D.

Furthermore, the injection hole 70 has a tapered surface, to thereby prevent extra air from being mixed into the other sealing material 17 when injecting the other sealing material 17. As a result, the reliability of the connection strength of the connection terminals 33 to the mounting terminals 40 is further improved.

Figure 9:
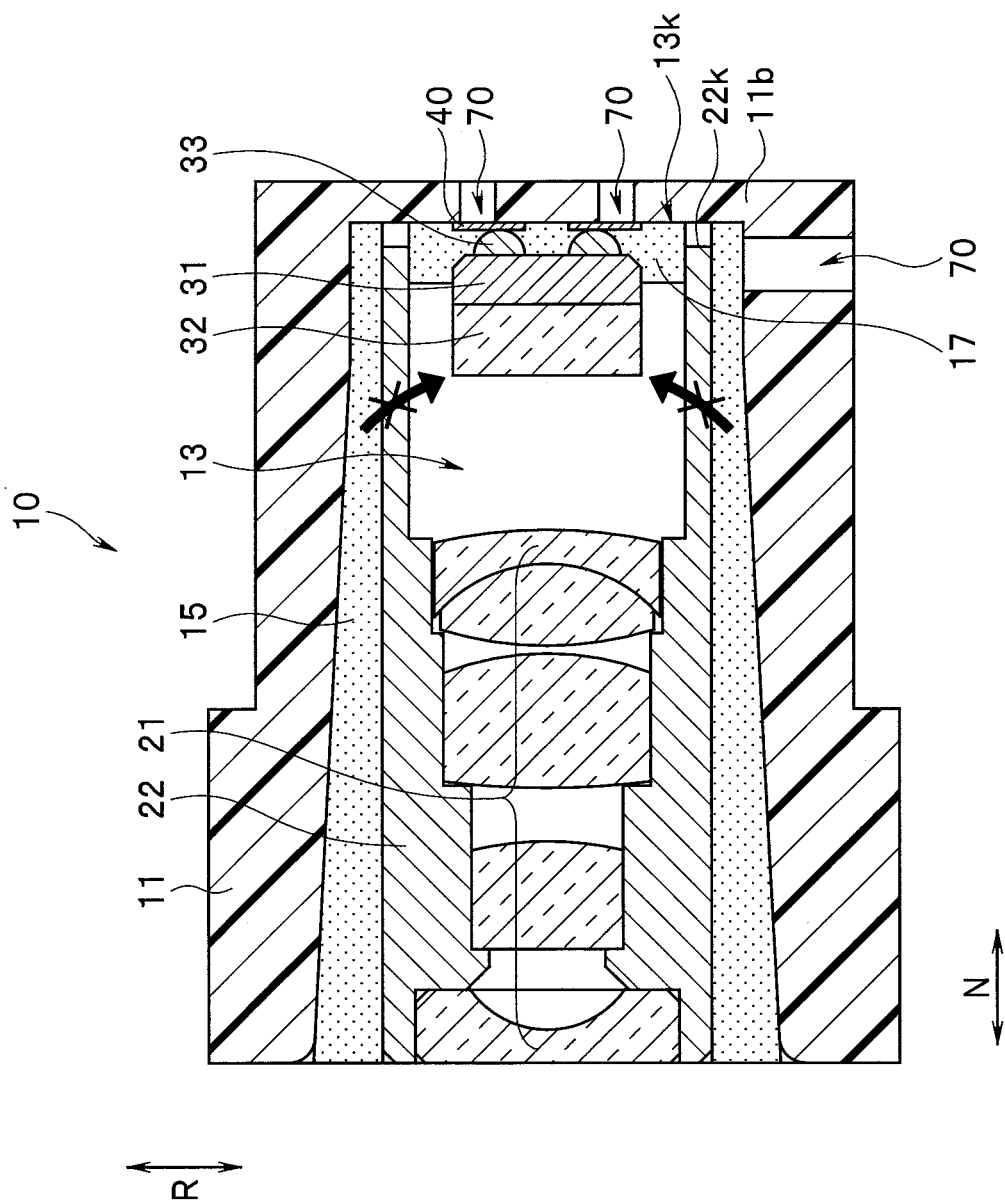
FIG. 9 is a cross-sectional view showing a modification in which an end portion of a lens frame in FIG. 2 is formed up to a bottom surface of the distal end member.

Next, description will be made on a modification of the shape of the lens frame 22, with reference to FIG. 9. FIG. 9 is a cross-sectional view showing the modification in which an end portion of the lens frame in FIG. 2 is formed up to the bottom surface of the distal end member.

As shown in FIG. 9, the lens frame 22 may be formed such that the outer diameter thereof on the bottom surface 13k side is larger in the radial direction R than that of the image pickup device unit 30. The lens frame 22 may be formed up to the bottom surface 13*k* in the longitudinal axis direction N. Note that the outer shape of the lens frame 22 covering the outer periphery of the image pickup device unit 30 may be a circular or rectangular shape.

Also in such a configuration, the other sealing material 17 is injected from the above-described injection holes 70 and 71 into the gap C2.

With such a configuration, even if the sealing material 15 injected in the gap C1 flows toward the bottom surface 13*k* side along the longitudinal axis direction N to fall down to the connection terminals 33 side, the periphery of the bonding surface D is covered with the lens frame 22, to thereby prevent the sealing material 15 from adhering to the bonding surface D. As a result, the separation of the bonding surface D can be prevented, as described above.

Furthermore, the sealing material 15 does not adhere to the cover glass 32, which prevents the deterioration of image quality.

In addition, it is possible to prevent extra external light from entering into the image pickup device 31, when positional adjustment of the objective lens unit 20 is performed in the recess portion 13.

Figure 10:
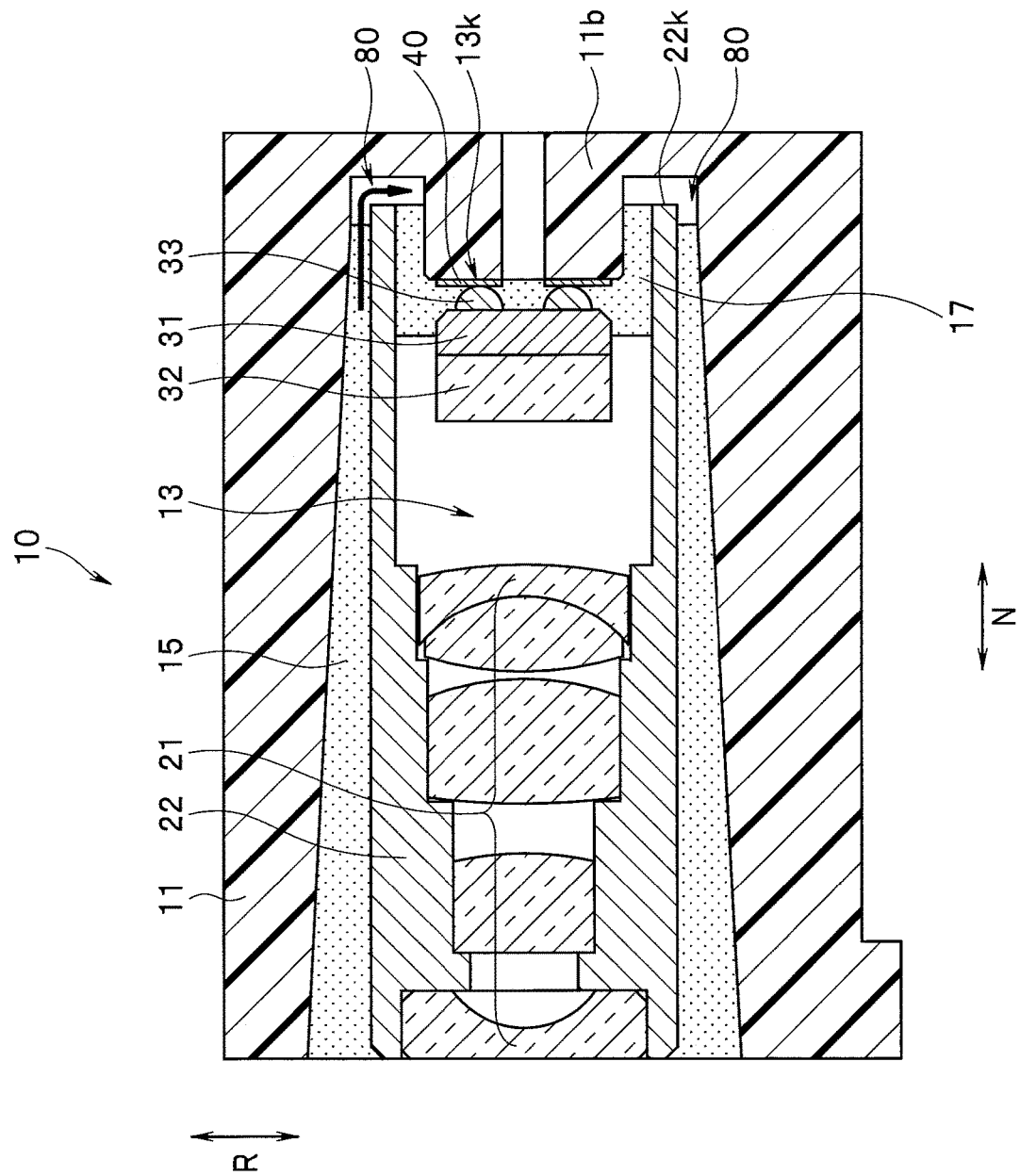
FIG. 10 is a cross-sectional view showing a modification of a shape of a bottom portion of the distal end member in FIG. 9.

Next, description will be made on a modification of the shape of the bottom portion 11*b* of the distal end member 11, with reference to FIG. 10. FIG. 10 is a cross-sectional view showing a modification of the shape of the bottom portion of the distal end member in FIG. 9.

As shown in FIG. 10, a groove 80, which is a holding frame housing space, is formed on the bottom surface 13*k* of the bottom portion 11*b*. The end portion 22*k* of the lens frame 22 may be fitted in the groove 80.

In other words, the groove portion 80 is formed on the bottom surface 13*k* so as to be recessed in the longitudinal axis direction N with respect to a surface on which the connection terminals 33 are connected.

Also in such a configuration, the other sealing material 17 is injected from the above-described injection holes 70 and 71 into the gap C2.

With such a configuration, even if the sealing material 15 injected in the gap C1 flows to the bottom surface 13*k* side along the longitudinal axis direction N, the flowed sealing material 15 is first pooled in the groove 80. Such a configuration can prevent the sealing material 15 from adhering to the cover glass 32 and the connection terminals 33 more surely than the above-described configuration shown in FIG. 9.

The adhering area of the lens frame 22 to the inner peripheral surface 13*n* of the recess portion 13 by using the sealing material 15 is further increased, which enables the lens frame 22 to be surely fixed. As a result, it is possible to surely prevent release of fixation of the lens frame 22 due to a stress or an impact on the distal end portion 2*s* when the bending portion 2*w* is bent, to thereby improve the reliability of the image pickup unit 10.

Furthermore, if the lens frame 22 is configured of an electromagnetic wave shielding member made of metal or the like, the lens frame 22 can prevent an influence of an electromagnetic wave from outside on the image pickup device 31, which enables an image with low noise to be acquired.

Figure 11:
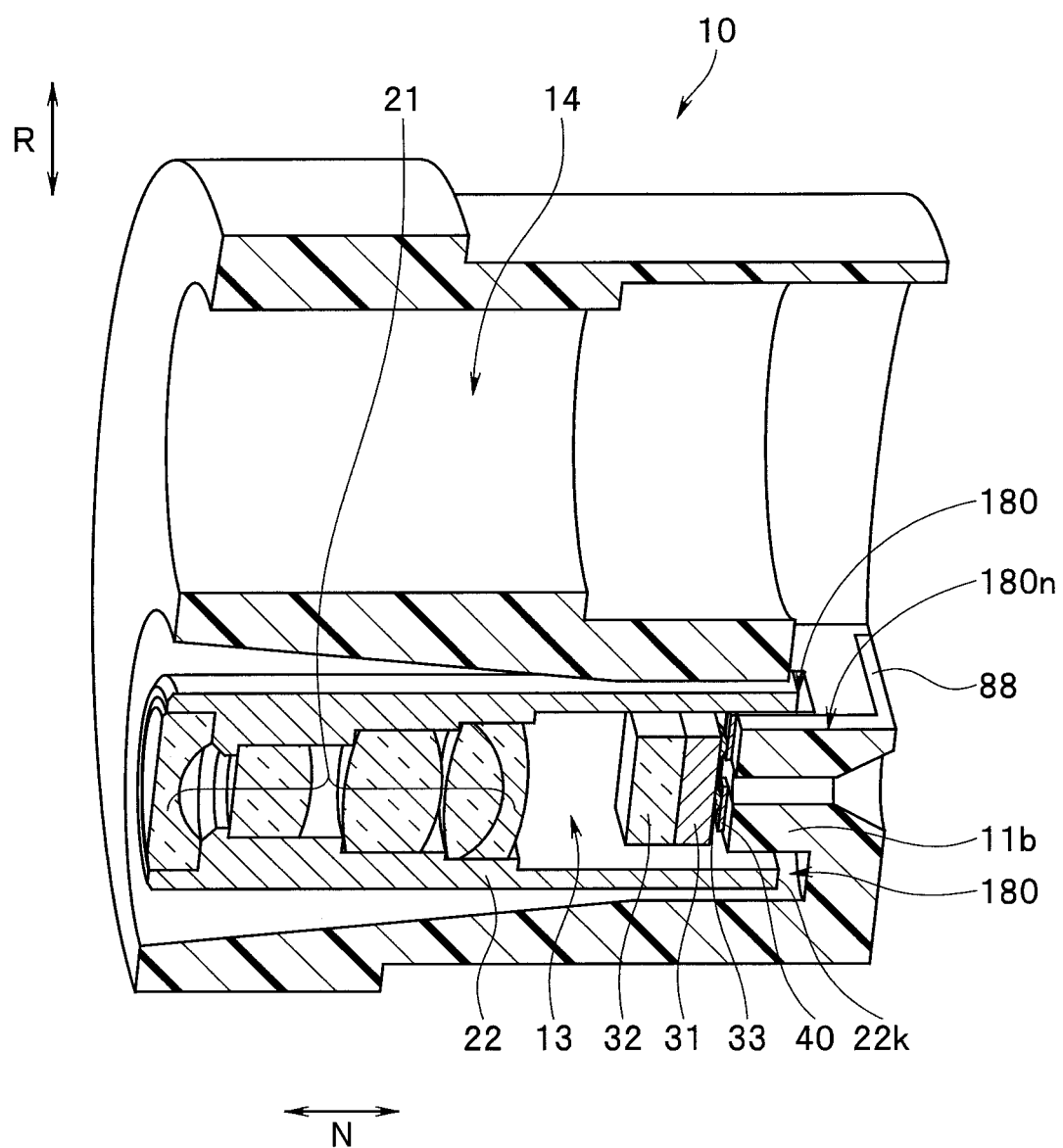
FIG. 11 is a perspective view showing a configuration in which the cable is connected to mounting terminals in FIG. 10 through a wiring, with a part of the distal end member shown in a cross section.

Next, with reference to FIG. 11, description will be made on a configuration in which the cable in FIG. 3 is connected to the mounting terminals in FIG. 10. FIG. 11 is a perspective view showing the configuration in which the cable is connected to the mounting terminals in FIG. 10 through a wiring, with a part of the distal end member shown in a cross section.

As shown in FIG. 11, the holding frame housing space formed at the bottom portion 11*b* of the distal end member 11 may be configured of a through hole 180 that penetrates the bottom portion 11*b* in the longitudinal axis direction N, and a wiring 88 formed by plating or the like, which is electrically connected to the mounting terminals 40, may be formed on an inner peripheral surface 180*n* of the through hole 180.

The signal line 51 of the cable 50 is electrically connected to the wiring 88, to thereby establish the electric connection between the mounting terminals 40 and the cable 50.

Note that the end portion 22*k* of the lens frame 22 is fitted in the through hole 180, similarly as in the configuration in FIG. 10.

The mounting terminals 40 and the cable 50 may be electrically connected to each other through a wiring in a through hole formed in the bottom portion 11*b*, other than the through hole 180 in which the end portion 22*k* of the lens frame 22 is fitted.

With such a configuration, signal transmission is possible in a short distance, compared with a configuration in which the wiring 88 is arranged along the inner peripheral surface 13*n* of the recess portion 13 of the distal end member 11. As a result, the signal transmission efficiency can be improved.

In addition, the region where the wiring 88 is formed can be reduced in the image pickup unit 10, which can achieve the reduction in the diameter size of the distal end member 11.

Figure 12:
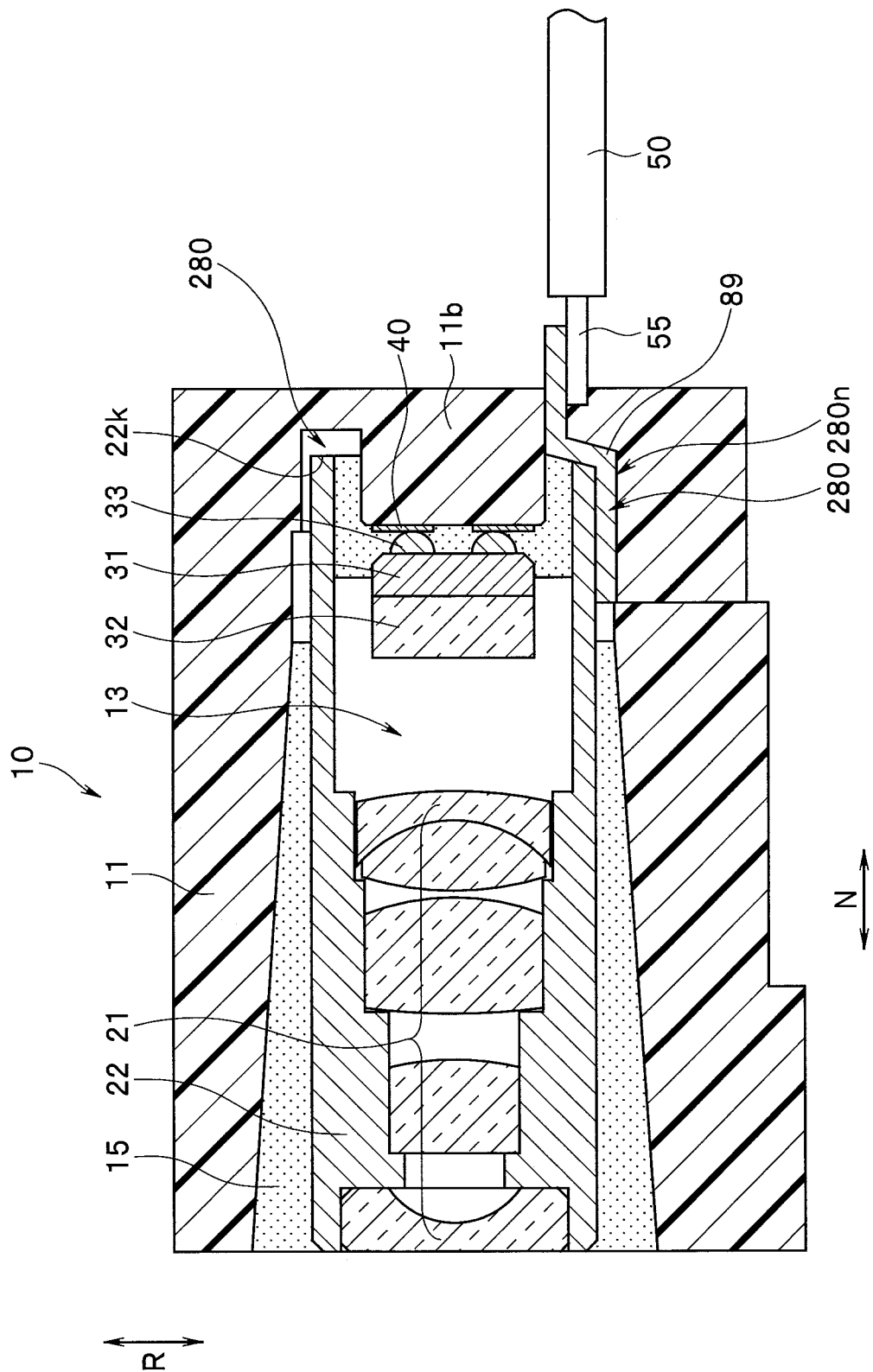
FIG. 12 is a cross-sectional view of the distal end member, which shows a configuration in which a ground (GND) terminal of the cable is connected to the lens frame in FIG. 10 through a wiring.

Next, with reference to FIG. 12, description will be made on a configuration in which a ground (GND) terminal of the cable in FIG. 3 is connected to the lens frame in FIG. 10. FIG. 12 is a cross-sectional view of the distal end member, which shows the configuration in which the GND terminal of the cable is connected to the lens frame in FIG. 10 through a wiring.

As shown in FIG. 12, a holding frame housing space formed in the bottom portion 11*b* of the distal end member 11 may be configured of a through hole 280 that penetrates the bottom portion 11*b* in the longitudinal axis direction N, and a GND wiring 89 formed by plating or the like, which is electrically connected to the lens frame 22, may be formed on an inner peripheral surface 280*n* of the through hole 280.

A GND terminal 55 of the cable 50 is electrically connected to the GND wiring 89, and thereby the lens frame 22 is insulated.

Note that, similarly as in the configurations shown in FIGS. 10 and 11, the end portion 22*k* of the lens frame 22 is fitted in the through hole 280.

Such a configuration can ensure a conduction path for releasing static electricity generated in the distal end member 11, through the lens frame 22, toward the operation portion 3 side of the insertion portion 2. In addition, since the image pickup device 31 and the connection terminals 33 are insulated, an influence by the static electricity on the image quality and driving of the image pickup device 31 can be eliminated.

Figure 13:
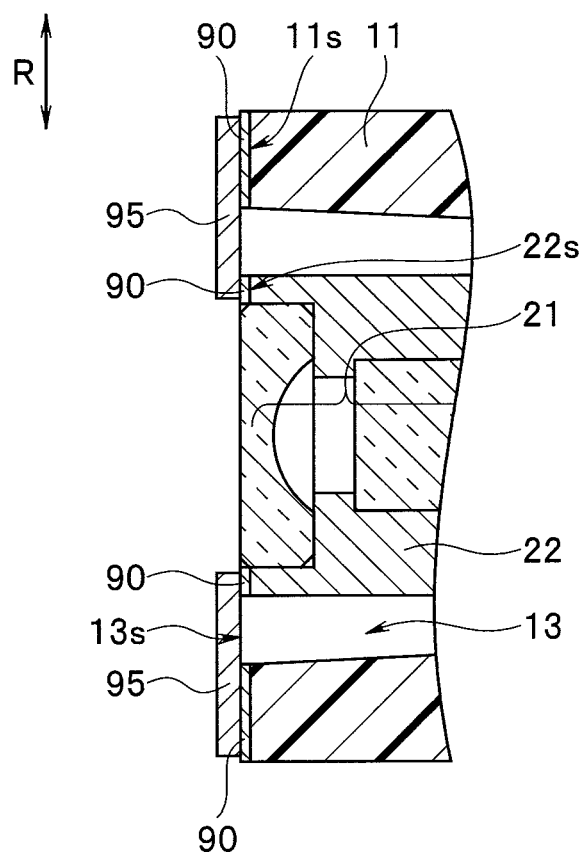
FIG. 13 is a partial cross-sectional view showing a modification of a configuration of an opening side of the distal end member in FIG. 2.

Next, a modification of the configuration of the opening 13*s* side of the distal end member 11 will be described with reference to FIG. 13. FIG. 13 is a partial cross-sectional view showing the modification of the configuration of the opening side of the distal end member in FIG. 2.

As shown in FIG. 13, metal members 90, such as plating, are formed respectively on a surface 11*s* of the distal end member 11 and a surface 22*s* of the lens frame 22. The surface 11*s* is a surface surrounding the opening 13*s*, and the surface 22*s* is positioned in substantially the same surface as the opening 13s. The respective metal members 90 may be metal-bonded to each other by solder or the like by a connecting member 95.

According to such a configuration, a gap in the radial direction R between the distal end member 11 and the lens frame 22, which is located on one end side of the distal end member 11, is sealed with the connecting member 95. Thus, the connecting member 95 can prevent intrusion of in-vivo residue, water, and moisture into the image pickup unit 10 in a use environment of the endoscope 1.

In other words, water-tightness, chemical resistance in cleaning and disinfecting, and air tightness in the image pickup unit 10 can be improved, and the fixing force of the lens frame 22 with respect to the distal end member 11 can be more improved.

The sealing material 15 is injected into the whole gap C1 and the sealing material 15 is heated to be cured. However, the material to be injected into the whole gap C1 may be another adhesive.

In the present embodiment, the image pickup unit 10 is configured such that the image pickup device unit 30 and the objective lens unit 20 are inserted into and fixed to the recess portion 13 of the distal end member 11 as an MID (molded interconnect device) on which various wirings are printed, and the cross-sectional area of the recess portion 13 increases continuously or stepwise from the bottom surface 13k toward the opening 13s. In addition, the objective lens unit 20 is fixed, by the sealing material 15, to the recess portion 13 at the set position where the focus adjustment is performed on the objective lens unit 20.

In such a configuration, the distal end member 11 as the MID is used, to thereby enable the image pickup device unit 30 and the objective lens unit 20 to be mounted directly to the distal end member 11. Therefore, assembling of the image pickup unit 10 having a configuration capable of transmitting and receiving signals to and from the cables and the like can be facilitated, and diameter reduction of the image pickup unit 10 can be achieved.

Furthermore, the objective lens unit 20 is directly assembled to the recess portion 13 where the objective lens unit 20 is optically adjusted and fixed.

Thus, the number of components constituting the distal end portion 2s can be reduced, and also the assembling processes can be reduced, which results in a cost reduction.

When the optical adjustment of the objective lens unit 20 is performed, the image pickup device 31 is driven, and the optical adjustment can be performed, with an image being outputted on the monitor, not shown. Therefore, shift adjustment of the optical axis position, focusing adjustment, field angle adjustment and the like can be performed with high accuracy.

Furthermore, in the conventional assembling of the image pickup unit 10, a known centered lens has been an essential component, and the optical design of the image pickup unit 10 has taken such a centered lens into consideration. In contrast, in the configuration according to the present embodiment, the image pickup unit 10 can be assembled without using a centered lens.

The recess portion 13 has a shape in which the spatial cross-sectional area thereof increases continuously or stepwise toward the opening 13s, with respect to the bottom surface 13k.

With such a configuration, in the positional adjustment of the objective lens unit 20 is performed, the space into which the grasping jig 100 enters and a clearance for performing optical axis adjustment of the objective lens unit 20 with respect to the image pickup device 31 can be provided between the recess portion 13 of the distal end member 11 and the objective lens unit 20. Furthermore, the thickness of the surface of the distal end member 11 on the recess portion 13 side can be increased toward the direction of the bottom surface 13k, to thereby enable the rigidity of the distal end member 11 to be increased.

With such a shape of the recess portion 13, a resin inflow property can be improved at the time of molding the distal end member 11, which leads to an improvement of the manufacturing yield.

Furthermore, the opening cross-sectional area of the opening 13s is larger than the surface area of the bottom surface 13k. Therefore, even in a case where the image pickup device unit 30 is tilted with respect to the bottom surface 13k, after the image pickup device unit 30 has been mounted to the bottom surface 13k, the optical axis adjustment of the image pickup device unit 30 with respect to the objective lens unit 20 can be performed, with the gap C1 for adhering with the sealing material 15 ensured in the recess portion 13.

In addition, in the recess portion 13, a taper angle of the objective lens unit 20 can be set in accordance with an amount of a worst tilt (optical axis tilt) assumed in the mounting process of the image pickup device unit 30.

Furthermore, the gap in which the sealing material 15 is injected becomes smaller toward the bottom surface 13k, the sealing material 15 hardly enter the image pickup device unit 30 side. Therefore, as described above, image failure as well as separation of the bonding surface D can be prevented, to thereby enable product quality to be improved.

In addition, in the case where the distal end member 11 is made by molding, if the tapered surface T is formed on the inner peripheral surface 13n of the recess portion 13, it becomes easy to release the distal end member from a mold.

As described above, it is possible to provide the image pickup unit 10 which enables diameter reduction and easy assembling and which has a configuration capable of preventing image failure and improving product quality, and the endoscope 1 including such an image pickup unit 10.

Second Embodiment

Figure 14:
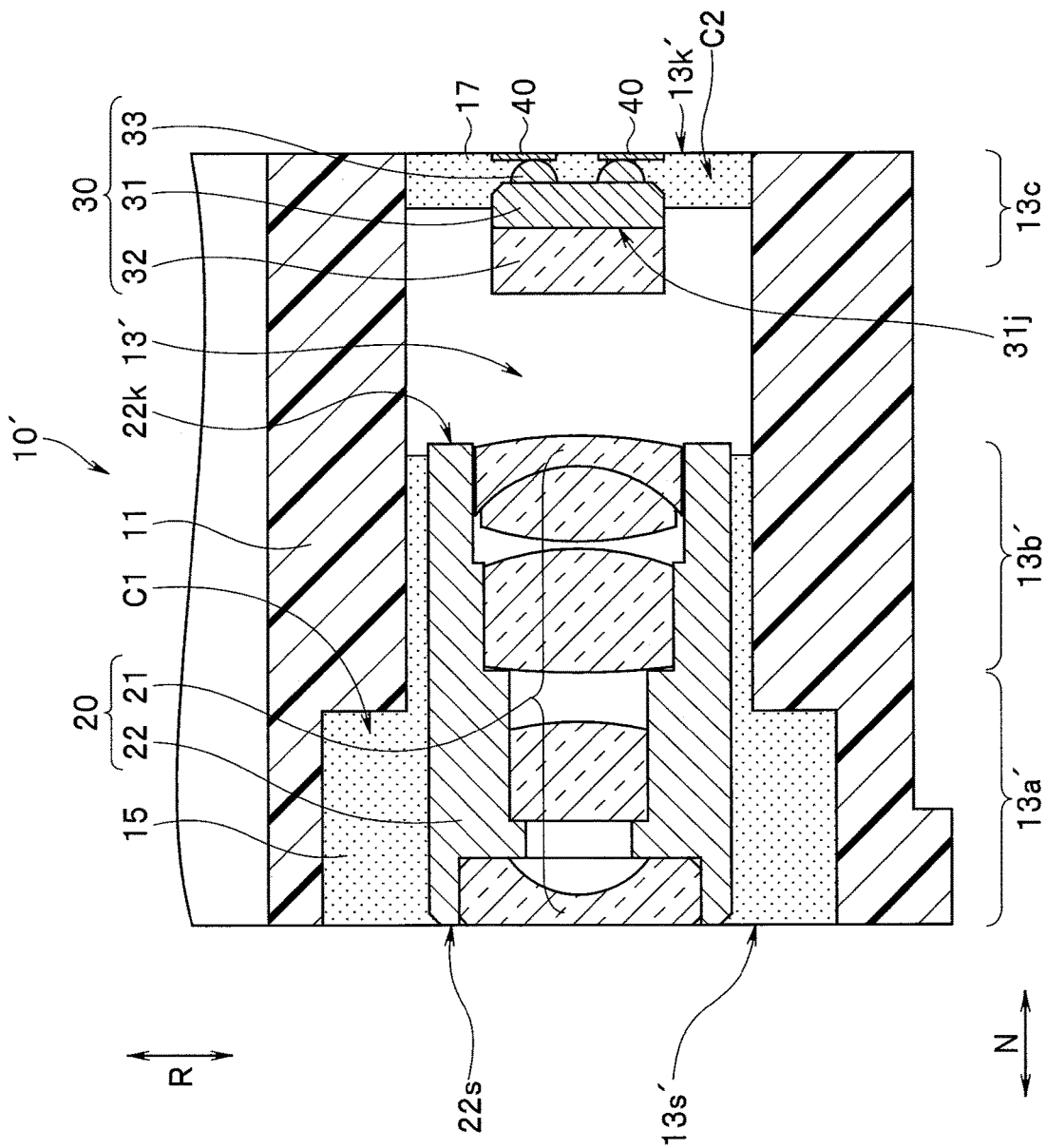
FIG. 14 is a cross-sectional view showing an outline of a configuration of an image pickup unit according to a second embodiment.
Figure 15:
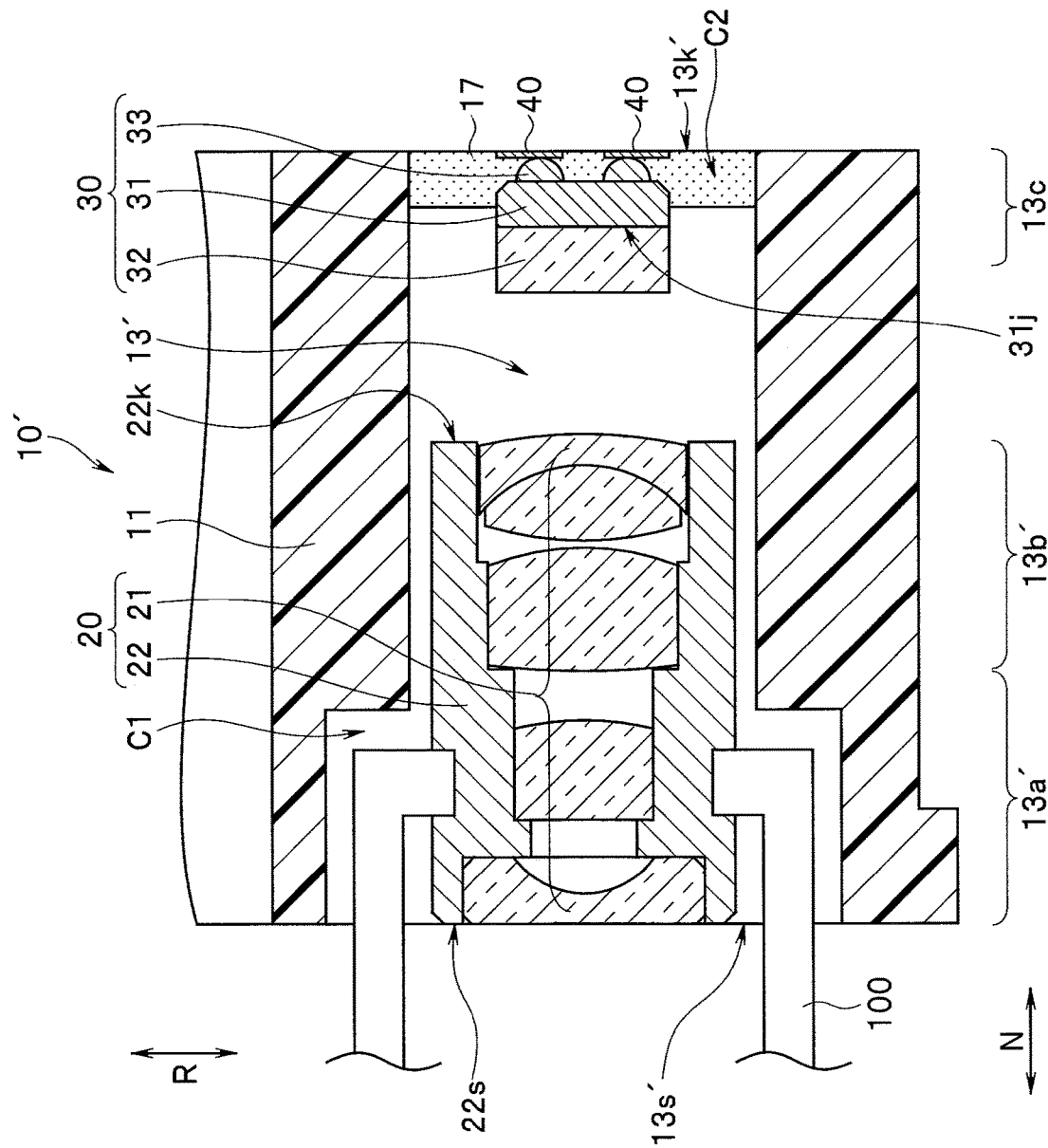
FIG. 15 is a partial cross-sectional view showing a state where an objective lens unit is inserted into a recess portion in the image pickup unit in FIG. 14 by using a grasping jig.

FIG. 14 is a cross-sectional view showing an outline of a configuration of an image pickup unit according to the present embodiment. FIG. 15 is a partial cross-sectional view showing a state where an objective lens unit is inserted into a recess portion in the image pickup unit in FIG. 14 by using a grasping jig.

Configurations of the image pickup unit and an endoscope according to the second embodiment are different in a shape of the recess portion from the image pickup unit and the endoscope according to the above-described first embodiment shown in FIGS. 1 to 13.

Only such a different point will be described, and the same components as those in the first embodiment are attached with the same reference signs and descriptions thereof will be omitted.

As shown in FIG. 14, an image pickup unit 10' according to the present embodiment is formed in a shape in which a spatial cross-sectional area of a recess portion 13' increases stepwise from a bottom surface 13k' toward an opening 13s'.

Specifically, the recess portion 13' includes a large-diameter region 13a', a small-diameter region 13b', and a terminal fixing region 13c.

The large-diameter region 13a' is formed, from the opening 13s' toward the bottom surface 13k', up to a middle position of an objective lens unit 20 in the longitudinal axis direction N. The objective lens unit 20 is fixed at a set position in the recess portion 13'.

In addition, the small-diameter region 13b' is formed, from the above-described middle position toward the bottom surface 13k', up to an end portion 22k of a lens frame 22, to be described later. The end portion 22k is an end portion of the objective lens unit 20 and faces the bottom surface 13k'.

In addition, in the present embodiment, only the large-diameter region 13a' is formed to have a diameter larger than that of the small-diameter region 13b' and that of the terminal fixing region 13c. The large-diameter region 13a' is formed to have a diameter which is constant in the longitudinal axis direction N, and also each of the small-diameter region 13b' and the terminal fixing region 13c has a diameter which is constant in the longitudinal axis direction N.

Note that other configurations are the same as those in the above-described first embodiment.

Also in the present embodiment, as shown in FIG. 15, a grasping jig 100 is inserted from the opening 13s' into the large-diameter region 13a' of the recess portion 13', in the state of grasping the lens frame 22 of the objective lens unit 20, to thereby allow the objective lens unit 20 to be disposed in the recess portion 13'.

Therefore, the large-diameter region 13a' configures a space into which the grasping jig 100 is inserted, when the objective lens unit 20 is housed and fixed to the set position in the recess portion 13'.

Note that other configurations and the assembling method of the image pickup unit 10 are the same as those in the above-described first embodiment.

With also such a configuration, the space for holding the lens frame 22 by the grasping jig 100 can be provided on the opening 13s' side in the recess portion 13'. Therefore, the same effects as those in the above-described first embodiment can be obtained.

Note that, in the first and second embodiments, the image pickup unit 10 has been described by taking the case where the image pickup unit 10 is provided in the endoscope 1. However, the image pickup unit is not limited to the case and it is needless to say that the image pickup unit may be provided in another insertion instrument.

Furthermore, the present invention is not limited to the above-described embodiments, but can be changed appropriately within a range not departing from the gist or concept of the invention that can be read from claims, throughout the specification, and the drawings.

What is claimed is:

1. An image pickup unit comprising:
   a housing comprising a recess including an opening at a distal end of the recess;
   a first sealing material disposed in the recess to form a bottom surface at a proximal end of the recess;
   an image sensor fixed to the bottom surface; and
   a frame comprising one or more lenses configured to form an image of light from an object on the image sensor, the frame being housed in the recess and fixed to the recess at a set position,
   wherein the recess is formed along a longitudinal axis direction such that a spatial cross-sectional area of the recess increases from the bottom surface toward the opening,
   the frame is fixed to the recess by a second sealing material injected in a radial gap between an exterior of the frame and an interior of the housing; and
   the first sealing material is separated from the second sealing material by a gap.

2. The image pickup unit according to claim 1, wherein the recess comprises:
   a large-diameter region formed, from the opening toward the bottom surface, up to a middle position of the frame in the longitudinal axis direction, the frame being fixed at the set position; and
   a small-diameter region formed, from the middle position toward the bottom surface, up to an end portion of the frame, and
   the frame is fixed in the recess by the second sealing material injected in the gap formed in the radial direction between an outer surface of the frame and the large-diameter and small-diameter regions.

3. The image pickup unit according to claim 2, wherein the large-diameter region and the small-diameter region are continuous in the longitudinal axis direction on an inner peripheral surface of the housing, to form a tapered surface, and form a spatial shape in which the spatial cross-sectional area increases continuously toward the opening.

4. The image pickup unit according to claim 2, wherein the image sensor is fixed at an image forming position of the one or more lenses, the image sensor further comprises a sealing glass fixed on a light-receiving surface of the image sensor, and a connection terminal provided to the image sensor on a side opposite to the sealing glass in the longitudinal axis direction, and the image sensor is fixed to the bottom surface by the connection terminal being electrically connected to a mounting terminal provided on the bottom surface, the recess further includes a terminal fixing region formed up to the bottom surface, on a side closer to the bottom surface than the small-diameter region, and
   the first sealing material is injected in a gap formed in the radial direction between an inner peripheral surface of the terminal fixing region and a part where the connection terminal and the mounting terminal are provided.

5. The image pickup unit according to claim 4, wherein the first sealing material has a filled surface on a side of the opening in the longitudinal axis direction, and the filled surface is located on a side closer to the bottom surface in the longitudinal axis direction than a bonding surface of the image pickup device and the sealing glass.

6. The image pickup unit according to claim 4, wherein the housing comprising an injection hole through which the first sealing material is injected into the recess, the injection hole being open on at least one of the bottom surface and the terminal fixing region in the recess.

7. The image pickup unit according to claim 6, wherein the injection hole is formed in a part where the terminal fixing region is formed in the housing, and a position of the injection hole, which is on a side of the opening in the longitudinal axis direction, is located on a side closer to the bottom surface in the longitudinal axis direction than a bonding surface of the image pickup device and the sealing glass.

8. The image pickup unit according to claim 7, wherein the injection hole is formed in a shape in which a cross section of an opening of the injection hole increases toward an outer peripheral surface of the housing.

9. The image pickup unit according to claim 2, wherein the large-diameter region configures a space into which a grasping jig is inserted when the frame is housed in the set position in the recess.

10. The image pickup unit according to claim 1, wherein the frame is formed so as to have a diameter larger than a diameter of the image sensor.

11. The image pickup unit according to claim 10, wherein
a frame housing space is formed on the bottom surface toward the other end in the longitudinal axis direction, and
at least a part of the frame is fitted in the frame housing space.

12. The image pickup unit according to claim 11, wherein
the frame housing space is configured of a through hole that penetrates the bottom surface along the longitudinal axis direction, and
a wiring is formed on an inner peripheral surface of the through hole, the wiring being electrically connected to the image sensor and electrically connected to a cable which is configured to transmit and receive a signal to and from the image sensor.

13. The image pickup unit according to claim 11, wherein
the frame housing space is configured of a through hole that penetrates the bottom surface along the longitudinal axis direction, and
a GND wiring insulated from the image sensor is formed on an inner peripheral surface of the through hole, the GND wiring being configured to electrically connect the frame and a GND terminal of a cable configured to transmit and receive a signal to and from the image sensor.

14. The image pickup unit according to claim 1, further comprising:
metal members each formed on a surface of the housing, which surrounds the opening located on the one end, and on a surface of the frame, which is located in substantially a same surface as the opening, and
the metal member of the housing and the metal member of the frame are metal-bonded by a connecting member.

15. The image pickup unit according to claim 1, wherein the gap is a longitudinal gap between a proximal surface of the second sealing material and a distal surface of the first sealing material.

16. The image pickup unit according to claim 15, wherein the frame and image sensor are separated by the longitudinal gap such that the frame and image sensor are independently positioned relative to each other within the recess.

17. The image pickup unit according to claim 1, wherein the gap is a radial gap between an inner surface of the second sealing material and an outer surface of the first sealing material.

18. An insertion instrument comprising:
an image pickup unit comprising:
a housing comprising a recess including an opening at a distal end of the recess;
a first sealing material disposed in the recess to form a bottom surface at a proximal end of the recess;
an image sensor fixed to the bottom surface; and
a frame comprising one or more lenses configured to form an image of light from an object on the image sensor, the frame being housed in the recess and fixed to the recess at a set position,
wherein the recess is formed along a longitudinal axis direction such that a spatial cross-sectional area of the recess increases from the bottom surface toward the opening,
the frame is fixed to the recess by a second sealing material injected in a radial gap between an exterior of the frame and an interior of the housing; and
the first sealing material is separated from the second sealing material by a gap.

19. The insertion instrument according to claim 18, wherein the gap is a longitudinal gap between a proximal surface of the second sealing material and a distal surface of the first sealing material.

20. The insertion instrument according to claim 18, wherein the gap is a radial gap between an inner surface of the second sealing material and an outer surface of the first sealing material.

\* \* \* \* \*